United States Patent
Dean et al.

(10) Patent No.: US 6,562,301 B1
(45) Date of Patent: May 13, 2003

(54) VESSEL CENTERING SYSTEM AND METHOD

(75) Inventors: Stephen D. Dean, Cary, NC (US); C. J. Anthony Fernando, Durham, NC (US); James E. Swon, Chapel Hill, NC (US)

(73) Assignee: Varian, Inc., Palo Alto, CA (US)

( * ) Notice: Subject to any disclaimer, the term of this patent is extended or adjusted under 35 U.S.C. 154(b) by 326 days.

(21) Appl. No.: 09/697,963

(22) Filed: Oct. 27, 2000

(51) Int. Cl.⁷ .............................. B01L 3/02; B01L 3/00; G01N 21/00; G01N 31/00; G04C 1/12; G04C 23/00
(52) U.S. Cl. .................. 422/102; 422/99; 422/100; 422/63; 220/640; 220/655
(58) Field of Search .................. 422/99, 102, 63, 422/100; 220/640, 655, 542, 234, 235, 253, 264

(56) References Cited

U.S. PATENT DOCUMENTS

| | | | |
|---|---|---|---|
| 150,204 A | * 4/1874 | Sunderland | 220/640 |
| 156,595 A | * 11/1874 | Roe | 220/640 |
| 269,143 A | * 12/1882 | Walls | 220/477 |
| 289,974 A | * 12/1883 | Carpenter | 220/641 |
| 1,179,188 A | * 4/1916 | Kaminski | 292/256.67 |
| 1,268,550 A | * 6/1918 | Dunlap | 220/320 |
| 2,575,446 A | * 11/1951 | Gollong | 220/319 |
| 2,628,739 A | * 2/1953 | Vischer | 220/305 |
| 2,691,460 A | * 10/1954 | Barnebey | 220/232 |
| 2,714,469 A | * 8/1955 | Carlson | 220/320 |
| 3,092,704 A | 6/1963 | De Woody | |
| 3,387,741 A | * 6/1968 | Kulaszewski | 220/655 |
| 3,559,844 A | * 2/1971 | Schlosberg | 220/565 |
| 3,587,700 A | * 6/1971 | Mauer | 220/732 |
| 5,080,232 A | 1/1992 | Leoncavallo et al. | |
| 5,190,209 A | * 3/1993 | Gordon et al. | 229/5.7 |
| 5,198,109 A | 3/1993 | Hanson et al. | |
| 5,296,139 A | 3/1994 | Hanson et al. | |
| 5,403,090 A | 4/1995 | Hofer et al. | |
| 5,589,649 A | 12/1996 | Brinker et al. | |
| 5,639,953 A | 6/1997 | Renslow | |

FOREIGN PATENT DOCUMENTS

| | | |
|---|---|---|
| EP | 0 976 453 A | 2/2000 |
| GB | 992 744 A | 5/1965 |
| GB | 2 001 032 A | 1/1979 |
| WO | WO 92/10294 | 6/1992 |

OTHER PUBLICATIONS

"Dissolution/General Requirements", USP 23–NF 18, Section <711> Dissolution, Ninth Supplement, Nov. 15, 1998, pp. 4660–4669.

* cited by examiner

Primary Examiner—Jill Warden
Assistant Examiner—Brian R Gordon
(74) Attorney, Agent, or Firm—Jenkins & Wilson, PA (57) ABSTRACT

A vessel centering system comprises a vessel, an annular, spacer member, a fastening element, and an elastometric component. The vessel includes an outer surface and a vessel groove formed on a circumference of the vessel outer surface. The spacer member is fitted in the vessel groove and extends outwardly with respect to the vessel. The first and second lateral end surfaces define a spacing therebetween. The spacer member includes a tangential bore and an annular groove. The tangential bore extends along a line generally tangential to a curvature of the spacer member. The fastening element, which could be a screw, is disposed in the tangential bore in engagement with the ring member and extends across the ring spacing. The elastometric component, which could be a gasket or O-ring, is disposed in the annular groove. A plurality of biased bearings can be provided instead of the elastometric component. When the vessel is installed in the aperture of a vessel plate, concentricity between the inner surfaces of the vessel and a shaft extending into the vessel is easily obtained.

19 Claims, 7 Drawing Sheets

VESSEL CENTERING SYSTEM AND METHOD

TECHNICAL FIELD

The present invention generally relates to the preparation or testing of sample substances contained in vessels in which stirring devices or other instruments operate. More particularly, the present invention relates to the centering and alignment of such vessels with respect to the stirring device.

BACKGROUND ART

In the pharmaceutical industry, the stirring or agitation of sample drugs or other substances in vessels is an important step in sample preparation procedures. Examples of such procedures include those performed for the purpose of testing and analyzing the rate at which doses release from pharmaceutical products, such as tablets or capsules, under controlled conditions. The procedural steps, test duration, dissolution medium, and apparatus employed in dissolution tests typically must comply with established, well-recognized guidelines, such as those promulgated by United States Pharmacopeia (USP), in order for the test to be accepted as valid for the specific substance tested.

The apparatus utilized for carrying out dissolution testing typically includes a vessel plate having an array of apertures into which test vessels are mounted. When the procedure calls for heating the media contained in the vessels, a water bath is often provided underneath the vessel plate such that each vessel is at least partially immersed in the water bath to enable heat transfer from the heated bath to the vessel media. In one exemplary type of test configuration (e.g., USP-NF Apparatus 1), a cylindrical basket is attached to a metallic drive shaft and a pharmaceutical sample is loaded into the basket. One shaft and basket combination is manually or automatically lowered into each test vessel mounted on the vessel plate, and the shaft and basket are caused to rotate. In another type of test configuration (e.g., USP-NF Apparatus 2), a blade-type paddle is attached to each shaft, and the pharmaceutical sample is dropped into each vessel such that it falls to the bottom of the vessel. When proceeding in accordance with the general requirements of Section <711>(Dissolution) of USP24-NF19, each shaft must be positioned in its respective vessel so that its axis is not more than 2 mm at any point from the vertical axis of the vessel.

It is therefore an important criterion in certain uses of vessels in which shafts operate that the vessel, and especially its inner surfaces, be aligned concentrically with respect to the shaft, and various approaches have heretofore been taken to assist in meeting this criterion.

One approach is disclosed in U.S. Pat. No. 5,403,090 to Hofer et al., in which at least two embodiments of a vessel aligning structure are provided to lock a standard USP dissolution test vessel into a stable, centered position in a vessel plate relative to a stirring shaft. The vessel is extended through one of the apertures of the vessel plate such that the flanged section of the vessel rests on the top of the vessel plate.

In one embodiment disclosed in U.S. Pat. No. 5,403,090, the vessel aligning structure includes an annular ring having a tapered cylindrical section depending downwardly against the inner surface of the vessel, and an annular gasket surrounding the annular ring. When the vessel aligning structure is pressed onto the vessel, the annular gasket is compressed between the vessel aligning structure and the flanged section of the vessel. A mounting receptacle is secured to the vessel plate adjacent to each aperture of the vessel plate. The vessel aligning structure further includes a horizontal bracket arm which slides into the mounting receptacle and is secured by a wing nut and associated threaded stud. The bracket arm also supports the mounting assembly for the motor and stirring shaft associated with that particular vessel location of the vessel plate.

In another embodiment disclosed in U.S. Pat. No. 5,403,090, the vessel aligning structure includes a plurality of mounting blocks secured to the vessel plate. One mounting block is positioned over each aperture of the vessel plate. Each mounting block includes a tapered cylindrical section depending downwardly against the inner surface of the vessel. The mounting block has two alignment bores which fit onto corresponding alignment pegs protruding upwardly from the vessel plate.

Another approach to vessel alignment is disclosed in U.S. Pat. No. 5,589,649 to Brinker et al, in which each aperture of a vessel plate is provided with three alignment fixtures circumferentially spaced in 120 degree intervals around the aperture. Each alignment fixture includes two semi-rigid alignment arms or prongs extending into the area above the aperture. The flanged section of the vessel rests on top of the alignment arms, such that each pair of alignment arms contact the outer surface of the vessel and the vessel is thereby supported by the alignment fixtures. The alignment arms are described as exerting compressive or "symmetrical spring" forces that tend to center the vessel within the aperture of the vessel plate in which the vessel is installed in order to align the vessel with respect to a stirring element.

Many current vessel centering systems require an unacceptably large footprint around the vessels of a dissolution testing apparatus. As acknowledged by those skilled in the art, a vessel centering system that takes up less area would permit the design of a smaller overall apparatus. The use of a smaller apparatus would be highly desirable in view of the costs associated with building and maintaining pharmaceutical laboratory space.

In addition, current vessel centering systems require the manipulation of two or more components to account for the often poor and/or inconsistent manufacturing tolerances observed in the wall thickness of the extruded glass tubing from which vessels are formed and in the vessel manufacturing process itself. As noted in the publication "Dissolution Discussion Group®," Vol. 1, Section 29.2 (VanKel Technology Group, 1999), glass vessels can be made by hand from large-bore glass tubing. The glass tubing is placed in a rotating device similar to a lathe, heat is applied, and the tubing is separated and sealed to form a hemispheric or other shaped bottom section. Heat is continually applied while the vessel is blown into the desired shape. This labor-intensive process can result in dimensional irregularities in the finished glass product. While plastic vessels are manufactured with better tolerances since they are fashioned from molds, plastic vessels are generally less desirable in many applications due to drug affinity with the surface and slower heat-up rate. Accordingly, there presently exists a need for developing a vessel centering system that adequately addresses the poor tolerance issue.

It is believed that a continuing need exists for practical and effective solutions to providing a vessel centering system. The present invention is provided to address these and other problems associated with the centering and alignment of vessels.

DISCLOSURE OF THE INVENTION

The present invention generally provides a vessel centering or alignment system which establishes and maintains a high degree of concentricity between the inner surfaces of a vessel and its associated shaft. The invention finds advantageous utility in any application in which concentricity is desired as between a vessel and a shaft or other elongate instrument extended into and operating within the vessel. The invention is particularly useful in connection with a sample handling or dissolution apparatus in which one or more vessels are to be installed onto or into some type of a vessel plate or rack. The invention is broadly characterized as providing a vessel which has a structurally distinct, locking flanged section.

According to one embodiment of the present invention, a vessel is adapted for improved centering with respect to a spindle when such vessel is installed in a vessel plate. The vessel comprises a vessel wall, an annular, spacer member, and a fastening or locking element. The vessel wall includes an outer surface and a vessel groove formed on a circumference of the vessel outer surface. The spacer member is fitted in the vessel groove and extends outwardly with respect to the vessel wall, terminating at a first lateral end surface and a second lateral end surface. The fastening element engages the spacer member near the first and second lateral end surfaces.

According to another embodiment of the present invention, the spacer member includes an outer surface, a first lateral end surface, a second lateral end surface, a first tangential bore, and a second tangential bore. The first tangential bore extends from a first outer aperture of the spacer member outer surface to a first inner aperture of the first lateral end surface. The second tangential bore extends from a second outer aperture of the spacer member outer surface to a second inner aperture of the second lateral end surface. The first and second lateral end surfaces define a gap therebetween. The first and second tangential bores extend along a line generally tangential to a curvature of the spacer member. The fastening element is disposed in the first and second tangential bores. The fastening element extends through the first inner aperture, across the gap, and through the second inner aperture, such that the fastening element is movable along the generally tangential line of the first and second tangential bores to engage the spacer member and tighten or lock the spacer member in the vessel groove.

According to yet another embodiment of the present invention, a vessel centering system comprises a vessel, an annular, spacer member, a fastening element, and an elastometric component. The vessel includes an outer surface and a vessel groove formed on a circumference of the vessel outer surface. The spacer member is fitted in the vessel groove and extends outwardly with respect to the vessel, terminating at first and second lateral end surfaces. The first and second lateral end surfaces define a gap therebetween. The spacer member includes a tangential bore and an annular groove. The tangential bore extends along a line generally tangential to a curvature of the spacer member. The fastening element is disposed in the tangential bore in engagement with the spacer member and extends across the gap. The elastometric component is disposed in the annular groove.

According to a further embodiment of the present invention, a vessel centering system comprises a vessel including an outer surface and a vessel groove formed on a circumference of the vessel outer surface, an annular, C-shaped ring member fitted in the vessel groove and extending outwardly with respect to the vessel, and means for tightening the ring member against the vessel groove.

According to an additional embodiment of the present invention, a vessel centering system includes a radial extension element disposed in contact with a ring member fitted to a precision groove cut along an outer circumference of a vessel.

According to yet another embodiment of the present invention, a plurality of biased bearings are substituted for the elastometric component.

According to a still further embodiment of the present invention, the vessel centering system comprises means for presenting a vessel alignment surface for the vessel centering system.

According to an additional embodiment of the present invention, a vessel centering system comprises a vessel plate, a vessel, an annular, spacer member, and a mechanical contact element. The vessel plate includes a vessel plate aperture. The vessel plate aperture includes a first edge and a second edge which cooperatively define an annular shoulder. The vessel extends through the Vessel plate aperture, and includes an outer surface and a vessel groove formed on a circumference of the vessel outer surface. The spacer member is fitted in the vessel groove and disposed on the first edge of the vessel plate aperture. The spacer member terminates at a first lateral end surface and a second lateral end surface. The mechanical contact element is disposed in engagement with the spacer member at the first and second lateral end surfaces.

The present invention also provides a method for aligning a vessel concentrically with respect to a shaft extending into the vessel, wherein an annular member is fitted in a groove formed around an outer surface of a flangeless vessel body, thereby forming a multi-piece flanged vessel. The ring member is locked or tightened in the vessel groove by utilizing a fastening element engaging the ring member.

The present invention further provides a method for assembling a vessel centering system. A circumferential groove is formed on an outer surface of a flangeless vessel body. An annular, spacer member can be formed such that the spacer member terminates at a first lateral end surface and a second lateral end surface, with the first and second lateral end surfaces defining a gap therebetween. A tangential bore is formed in the spacer member such that the tangential bore extends along a line generally tangential to a curvature of the spacer member and includes two bore sections opposing each other across the gap of the spacer member. A fastening element is provided and is adapted to engage the spacer member at the tangential bore. The spacer member is fitted in the vessel groove to form a multi-piece flanged vessel. The spacer member is secured in the vessel groove by adjusting a position of the fastening element with respect to the tangential bore.

It is therefore an object of the present invention to provide a vessel centering system adapted to easily and quickly achieve concentricity as between the inner surfaces of a vessel and a stirring element or other spindle or shaft-type instrument inserted into the vessel.

It is another object of the present invention to provide a multi-piece flanged vessel wherein the flanged section is a separate, removable structural component.

It is a further object of the present invention to provide a flanged vessel wherein the flanged portion can be locked onto the vessel wall or removed therefrom.

It is yet another object of the present invention to provide a vessel adapted for improved installation with a vessel plate, such as a vessel plate typically provided with a liquid handling apparatus or dissolution testing apparatus.

Some of the objects of the invention having been stated hereinabove, other objects will become evident as the description proceeds when taken in connection with the accompanying drawings as best described hereinbelow.

DETAILED DESCRIPTION OF THE INVENTION

Figure 1:
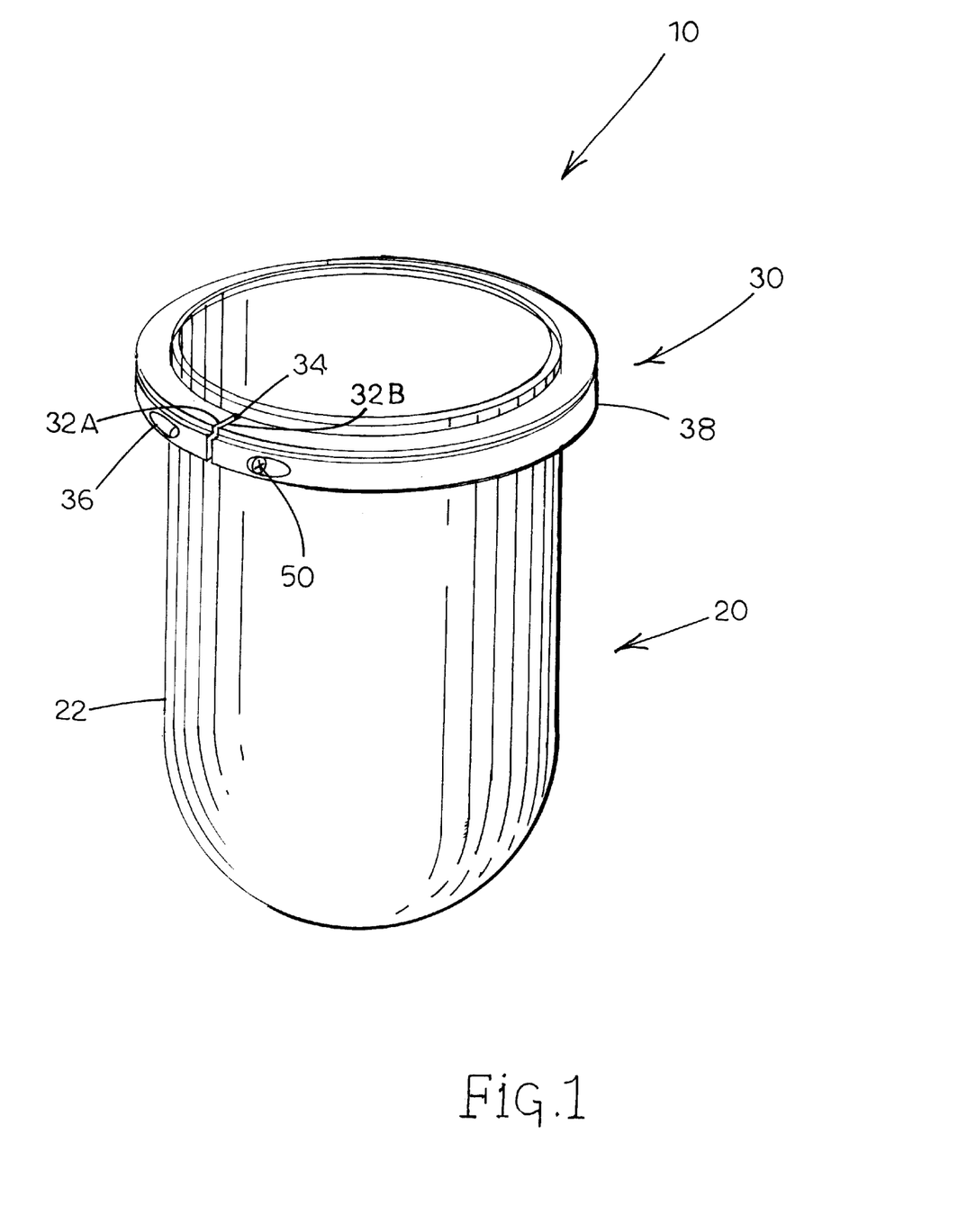
FIG. 1 is a perspective view of a vessel centering system provided according to the present invention.
Figure 2:
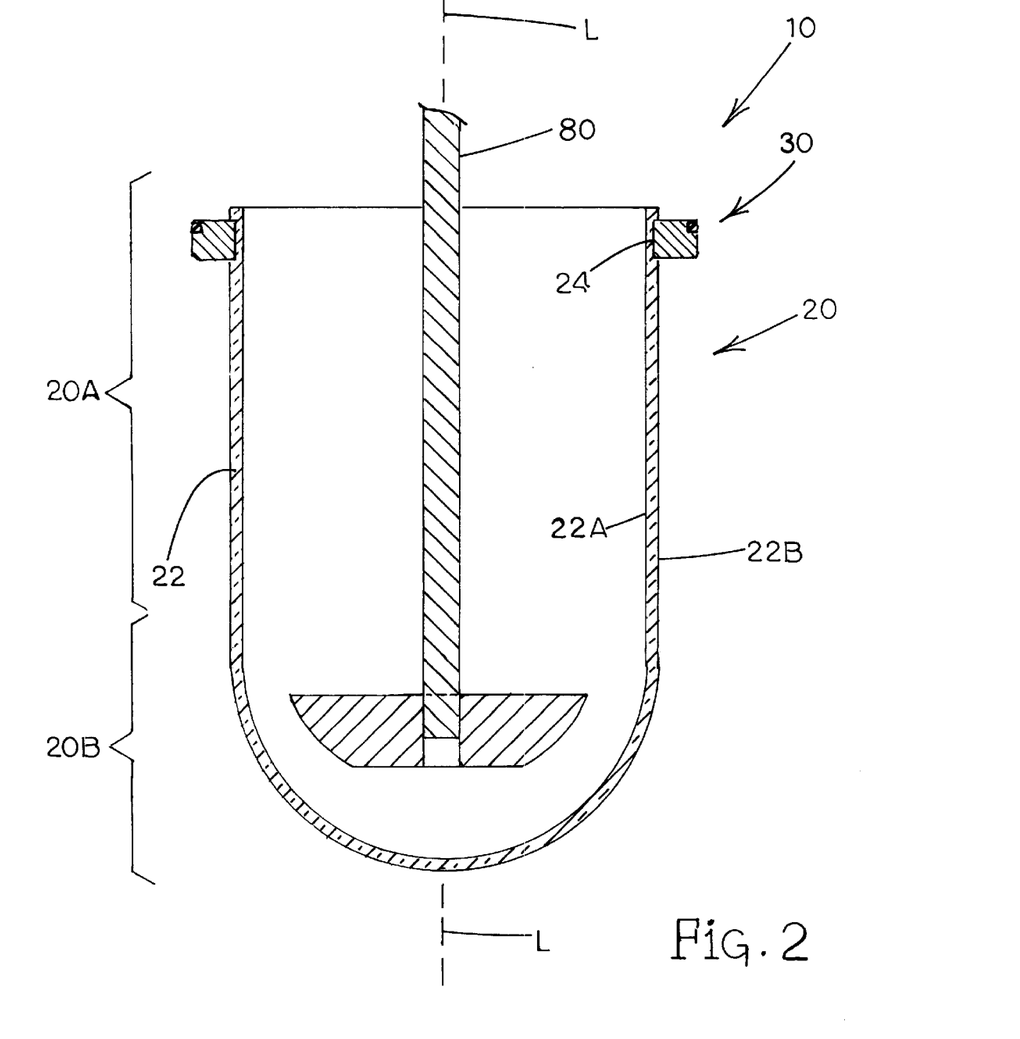
FIG. 2 is a vertical cross-sectional view of the vessel centering system illustrated in FIG. 1, and additionally of a shaft-based instrument operable in conjunction with the vessel centering system.
Figure 4:
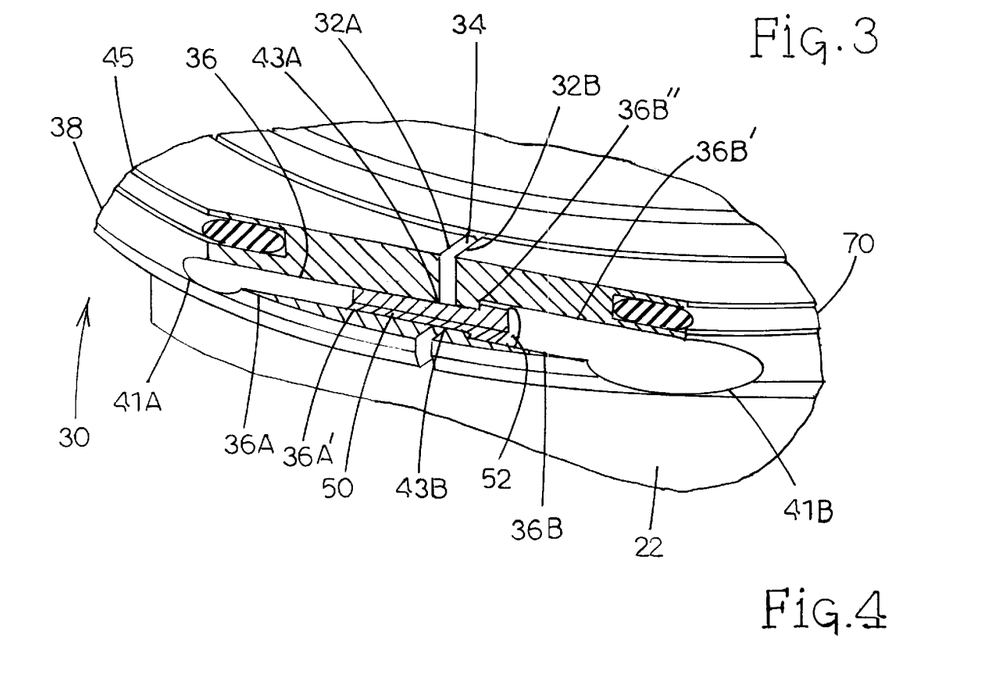
FIG. 4 is a detailed perspective and partial cutaway view of the vessel centering system illustrating an inner cross-sectional portion of a ring member provided according to the present invention.

Referring to FIGS. 1 and 2, a vessel centering/alignment system generally designated 10 is provided in accordance with the present invention, and is particularly suited for use in conjunction with a dissolution testing apparatus. Broadly stated, vessel centering system 10 includes a vessel generally designated 20 and a vessel alignment ring generally designated 30. Vessel 20 includes a vessel wall 22 having an inner surface 22A and an outer surface 22B. In the preferred embodiment, vessel 20 is a modification of a standard USP vessel having, for example, a lateral cylindrical section 20A and a bottom hemispherical section 20B (although bottom section 20B could be flat, dimpled, or have some other suitable configuration). Vessel alignment ring 30 serves as the flanged section of vessel 20, yet preferably is provided as a separate component such that vessel 20 could be characterized as having a multi-piece design. Vessel 20 is preferably constructed of a glass (or other transparent) material, and alignment ring 30 is preferably constructed of a polymeric material such as PVC or TEFLON material. Alignment ring 30 is C-shaped, and thus terminates at two lateral end surfaces 32A and 32B separated by a gap or ring spacing 34, as best shown in FIG. 4. As particularly shown in FIG. 2, an annular groove 24 is precision cut or ground into outer surface 22B of vessel wall 22 and is concentric with inner surface 22A. One way to properly form annular groove 24 relative to inner surface 22A is to chuck or attach a lathe to inner surface 22A, such that the lathe moves about a central, longitudinal axis L of vessel 20 as annular groove 24 is cut.

Alignment ring 30 is mounted in this annular groove 24. Annular groove 24 removes the irregularities that may be inherent in the extruded glass tubing or result from the glass manufacturing process. As will also become apparent from the present disclosure, vessel centering system 10 ensures concentricity as between inner surface 22A of vessel 20 and an instrument operative within vessel 20 such as a shaft-based agitator device 80, or any other device adapted for extension into vessel 20 along central axis L thereof. In addition, alignment ring 30 is designed for easy removal from vessel 20 either manually or by using a tool.

Referring to FIG. 4, a fastening or clamping means such as a tangential screw 50 is employed to squeeze, tighten, or otherwise secure alignment ring 30 into annular groove 24 and around the periphery of vessel 20, thus effectively locking alignment ring 30 into position with respect to vessel 20. To accommodate tangential screw 50, a tangential screw bore 36 is formed through the body of alignment ring 30 along a direction generally tangential to the curvature of alignment ring 30. In the exemplary embodiment shown, tangential bore 36.spans across gap 34 between lateral end surfaces 32A and 32B such that tangential bore 36 includes two generally aligned bore sections 36A and 36B. First bore section 36A extends between an outer surface 38 of alignment ring 30 and first lateral end surface 32A, and opens at an outer aperture 41A of outer surface 38 and at an inner aperture 43A of first lateral end surface 32A. Similarly, second bore section 36B extends between outer surface 38 of alignment ring 30 and second lateral end surface 32B, and opens at another outer aperture 41B of outer surface 38 and at an inner aperture 43B of second lateral end surface 32B.

It will be understood that tangential screw 50 is but one type of fastening element which could be adapted to operate within the context of the present invention. Other fasteners or clamps, now or later developed, may be found suitable for serving the same purpose or function as that of tangential screw 50. Preferably, second bore section 36B includes an enlarged diameter section 36B' to define a shoulder 36B" within second bore section 36B, and first bore section 36A includes a threaded section 36A' adapted to mate with the threads of tangential screw 50. In this manner, a suitable tool (not shown) can be inserted through second outer aperture 41B into second bore section 36B and brought into operative engagement with a head portion 52 of tangential screw 50. It will be understood that means other than a tool could be used to rotate tangential screw 50 or otherwise adjust its position relative to tangential bore 36. Because tangential screw 50 is forced into movable engagement with threaded section 36A' of first bore section 36A and its head portion 52 is forced into engagement with shoulder 36B" of second bore section 36B, rotation of tangential screw 50 acts to adjust the position of tangential screw 50 with respect to tangential bore 36, thereby adjusting the width of gap 34 and altering the outermost diameter and profile of alignment ring 30 to tighten or lock alignment ring 30 in place.

Figure 3:
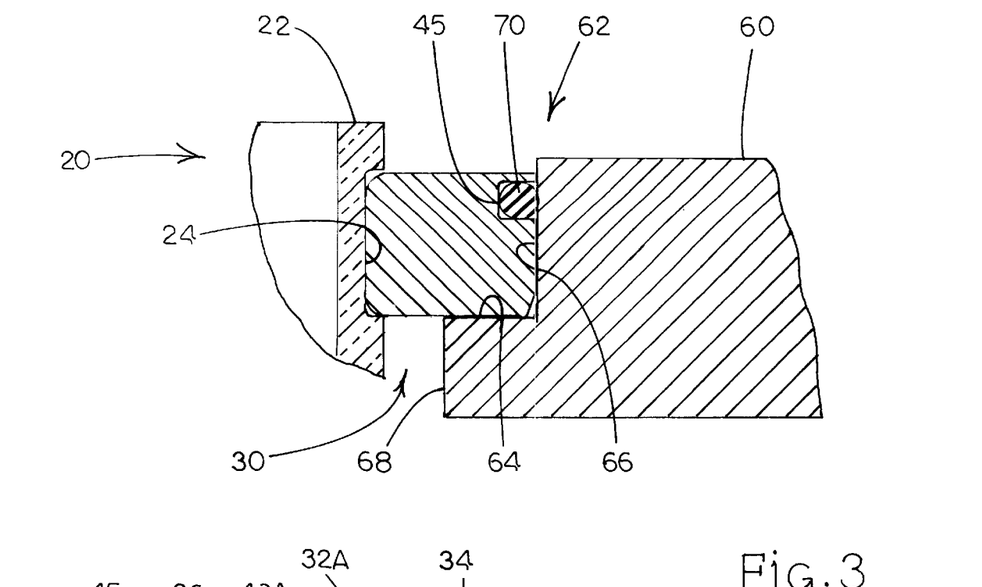
FIG. 3 is a detailed vertical cross-sectional and partial cutaway view of the vessel centering system installed on a vessel plate according to the present invention.

Referring to FIG. 3, vessel 20 is adapted to be installed in a vessel plate 60. In accordance with the present invention, vessel plate 60 includes one or more apertures, generally designated 62, which are modified to receive vessel 20. In this respect, modified vessel plate 60 could be considered as forming a part of vessel centering system 10. Each vessel plate aperture 62 is defined by a first edge 64 and a second edge 66 of vessel plate 60, which together define an annular shoulder 68 with which alignment ring 30 engages. Preferably, alignment ring 30 includes an annular groove 45, and a removable resilient or elastometric component 70 such as an annular gasket or O-ring (or other elastometric centering means) is fitted into annular groove 45 concentric with alignment ring 30 and vessel 20.

It can be seen that alignment ring 30 serves as a spacer means for bridging the annular gap presented between precision annular groove 24 and second edge 66 of vessel plate 60, and for establishing the concentricity of vessel 20 with respect to longitudinal axis L. At the same time, elastometric component 70 serves as an outer frictional surface or radial extension of vessel 20, and as a means for spanning the small (and potentially variable) annular gap presented between alignment ring 30 and the inner diameter of aperture 62 (i.e., second edge 66 of vessel plate 60). The use of elastometric component 70 thus enhances the establishment of the concentricity of vessel 20 with respect to longitudinal axis L and agitator device 80, rather than serving the conventional role of a seal. It can also be seen that the frictional outer surface presented by elastometric component 70 prevents vertical displacement of vessel 20 out of its installed position in vessel plate 60. This latter feature is advantageous in the situation where vessel or vessels 20 of vessel plate 60 have been immersed in a water bath, and the media content in one or more vessels 20 has been reduced to the point where vessel or vessels 20 are forcibly displaced upwardly due to buoyancy effects. Elastometric component 70 prevents its associated vessel 20 from "popping out" of vessel plate 60 in response to such buoyancy effects.

Figure 5:
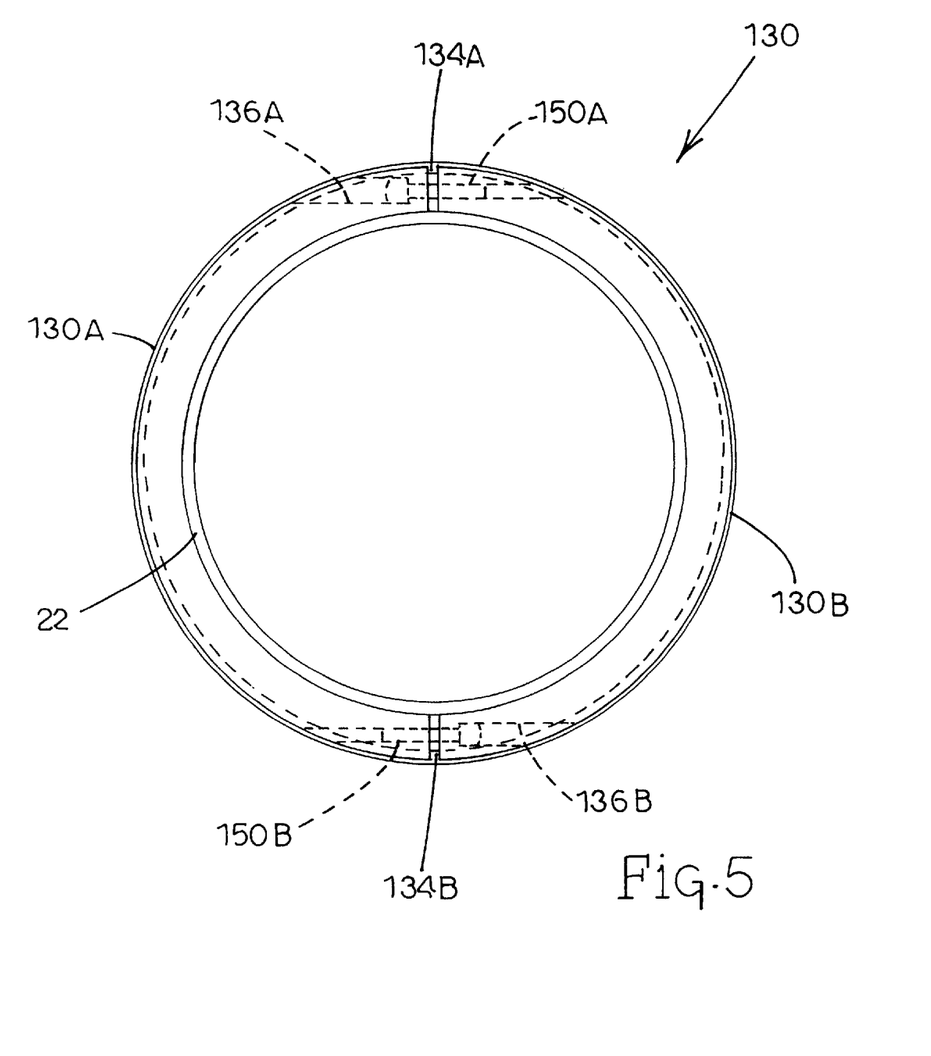
FIG. 5 is a top plan view of a spacer member or removable flange piece according to an embodiment of the present invention.

Referring to FIG. 5, an alternative embodiment of an alignment ring, generally designated 130, is illustrated according to the invention. FIG. 5 illustrates that the alignment ring of the present invention, as a spacer means and a means for ensuring concentricity, can assume configurations other than a C-ring such as alignment ring 30 discussed hereinabove. By way of example in FIG. 5, alignment ring 130 includes two or more segments 130A and 130B and accordingly defines two or more gaps or ring spacings 134A and 134B. In addition, two or more tangential bores 136A and 136B (with generally aligned bore sections and corresponding tangential screws 150A and 150B are provided.

Figure 6:
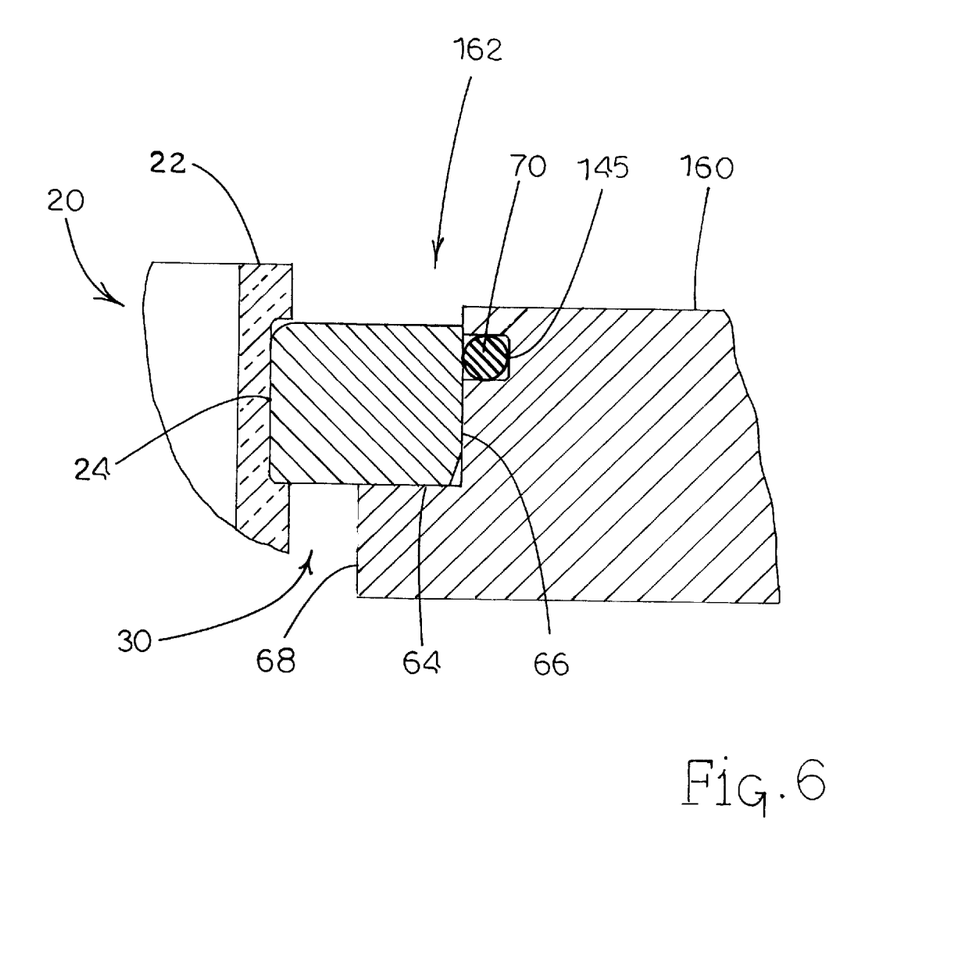
FIG. 6 is a detailed vertical cross-sectional and partial cut-away view of an alternative embodiment of the vessel centering system installed in a vessel plate.

Referring to FIG. 6, an alternate embodiment of the present invention is provided wherein an annular groove 145 is formed in a vessel plate aperture, generally designated 162, instead of being formed in alignment ring 30 shown in FIG. 3 (or alignment ring 130 shown in FIG. 5). Annular groove 145 extends into second edge 66 of a modified vessel plate 160. Elastomeric component 70 is fitted into annular groove 145. In this manner, elastomeric component 70 serves as an inner frictional surface of vessel plate aperture 162 to perform its gap-spanning and concentric positioning functions.

Figure 7A:
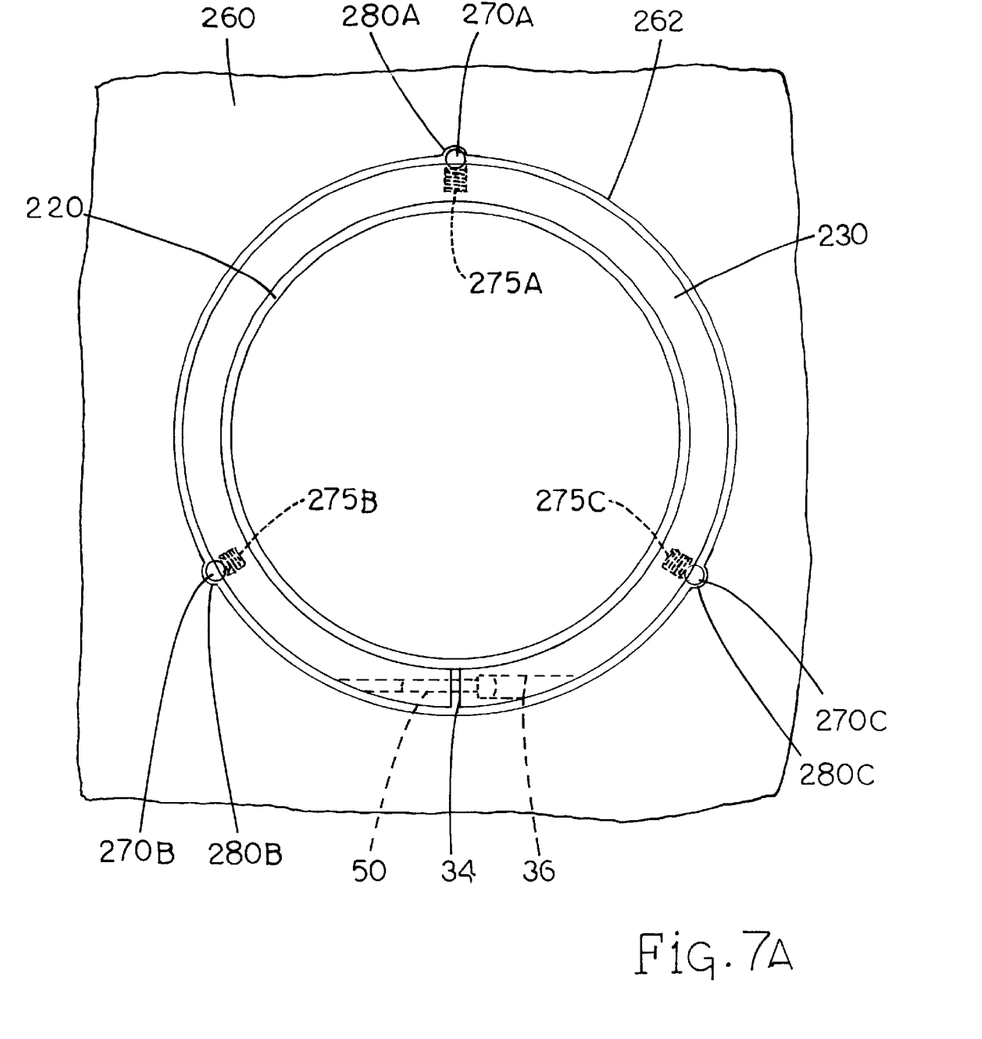
FIG. 7A is a top plan view of the vessel centering system according to one embodiment of the present invention wherein biased radial members are utilized.

Referring to FIG. 7A, an alternate embodiment of the present invention is provided wherein the gap-spanning and concentric positioning means take the form of radially outwardly biased (such as by spring loading) bearings or dimples 270A, 270B and 270C, instead of elastomeric component 70. By way of example, three bearings 270A, 270B and 270C are provided and are circumferentially spaced 120° from each other. Each bearing 270A, 270B and 270C and its associated biasing mechanism 275A, 275B and 275C are supported in or by a flanged section 230 (which can be integrally manufactured with a vessel 220 or provided as a separate, removable component as in other embodiments discussed above). Hence, bearings 270A, 270B and 270C extend outwardly from flanged section 230 and are biased to make contact with a vessel plate aperture 262 of a vessel plate 260 to establish the concentricity of vessel 220. In this embodiment, neither flanged section 230 nor aperture 262 require an annular gap 45 (see FIG. 3) or 145 (see FIG. 6). However, conformingly-shaped depressions or recesses 280A, 280B and 280C may be provided along the inner diameter of aperture 262 at the respective locations of bearings 270A, 270B and 270C to at least partially receive the outer profile of bearings 270A, 270B and 270C.

Figure 7B:
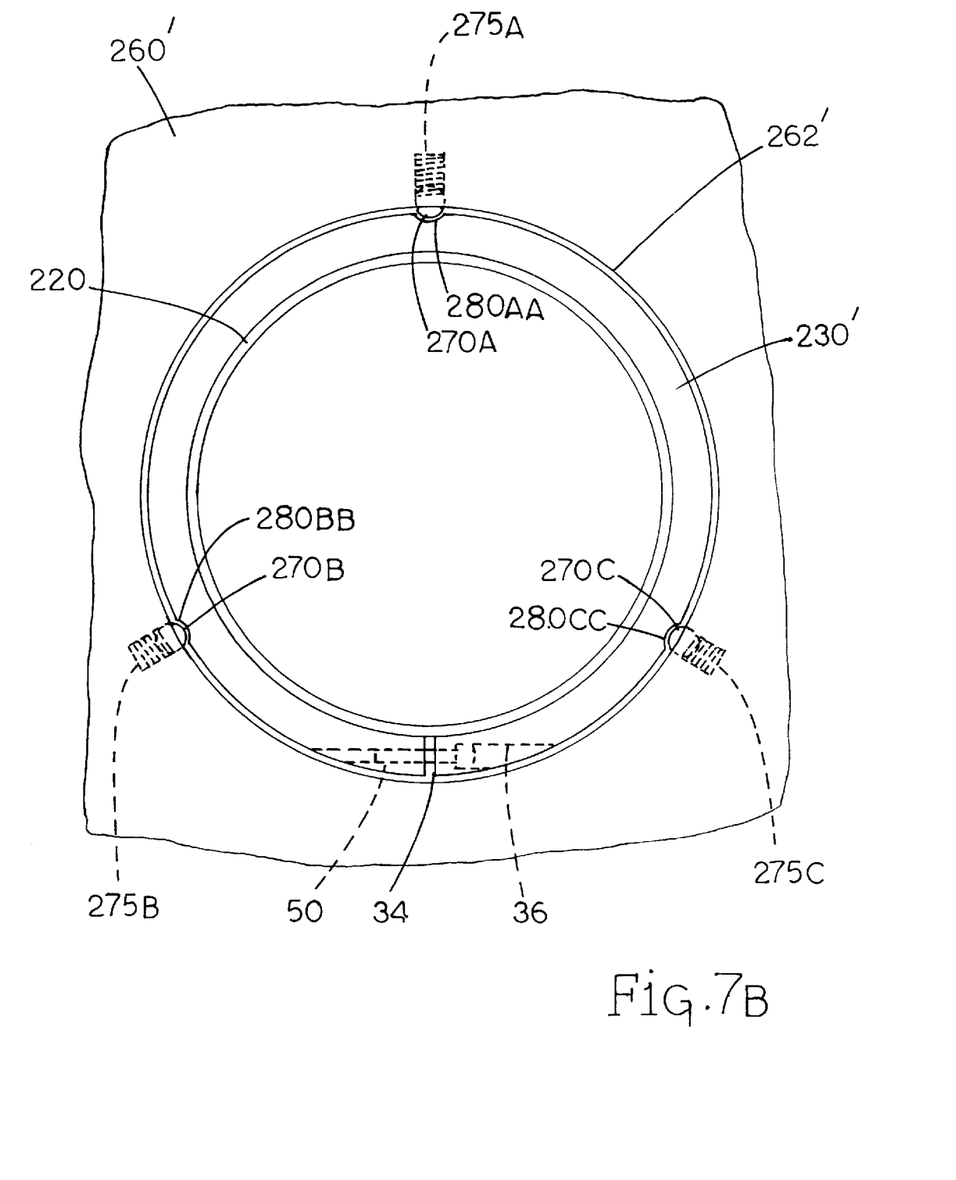
FIG. 7B is a top plan view of the vessel centering system according to another embodiment of the present invention wherein biased radial members are oriented differently from those radial members illustrated in FIG. 7A.

Referring to FIG. 7B, the respective orientations of bearings 270A, 270B and 270C and their associated biasing mechanisms 275A, 275B and 275C have been inverted such that they are radially inwardly biased toward a flanged section 230' (which can be integrally manufactured with vessel 220 or provided as a separate, removable component as in other embodiments discussed above). Each bearing 270A, 270B and 270C and its associated biasing mechanism 275A, 275B and 275C are supported in or by a vessel plate 260'. Hence, bearings 270A, 270B and 270C extend inwardly from an aperture 262' of vessel plate 260' and are biased to make contact with flanged section 230' to establish the concentricity of vessel 220. As in the embodiment illustrated in FIG. 7A, neither flanged section 230' nor aperture 262' require an annular gap 45 (or 145). However, conformingly-shaped depressions or recesses 280AA, 280BB and 280CC.may be provided along the outer diameter of flanged section 230' at the respective locations of bearings 270A, 270B and 270C to at least partially receive the outer profile of bearings 270A, 270B and 270C.

It can therefore be seen from the foregoing description that the present invention provides a useful system for centering and aligning a vessel with respect to a stirring element or other elongate instrument intended to operate within such vessel.

It will be understood that various details of the invention may be changed without departing from the scope of the invention. Furthermore, the foregoing description is for the purpose of illustration only, and not for the purpose of limitation-the invention being defined by the claims.

What is claimed is:

1. A vessel adapted for improved centering with respect to a spindle or other instrument when installed in a vessel plate, the vessel comprising:
    (a) a vessel wall including an outer surface and a vessel groove formed on a circumference of the vessel outer surface;
    (b) an annular spacer member fitted in the vessel groove and comprising a first lateral end surface and an opposing second lateral end surface, a radially outermost spacer member surface coaxial with the vessel outer surface, and a cross-section extending outwardly with respect to the vessel wall to the spacer member surface, the cross-section terminating at the first lateral end surface and the second lateral end surface, the first and second lateral end surfaces defining a gap therebetween; and
    (c) a fastening element engaging the first and second lateral end surfaces, extending across the gap, and disposed within the cross-section.

2. The vessel according to claim 1 comprising an elastomeric element disposed in contact with the spacer member.

3. The vessel according to claim 2 wherein the spacer member includes an annular groove opening outwardly with respect to the vessel wall and the elastomeric element is disposed in the annular groove.

4. The vessel according to claim 1 comprising a plurality of biased bearings attached to the spacer member.

5. The vessel according to claim 1 comprising a plurality of biased bearings disposed in contact with the spacer member.

6. A vessel adapted to be centered with respect to a spindle or other instrument when installed in a vessel plate, the vessel comprising:

(a) a vessel wall including an outer surface and a vessel groove formed on a circumference of the vessel outer surface;

(b) an annular spacer member fitted in the vessel groove and extending outwardly with respect to the vessel wall, the spacer member including a spacer member outer surface coaxial with the vessel outer surface, a first lateral end surface, a second lateral end surface opposing the first lateral end surface, a first tangential bore extending from a first outer aperture of the spacer member outer surface to a first inner aperture of the first lateral end surface, and a second tangential bore extending from a second outer aperture of the spacer member outer surface to a second inner aperture of the second lateral end surface, wherein the first and second lateral end surfaces define a gap therebetween, and wherein the first and second tangential bores extend along a line generally tangential to a curvature of the spacer member; and (c) a fastening element disposed in the first and second tangential bores, the fastening element extending through the first inner aperture, across the gap, and through the second inner aperture, wherein the fastening element is movable along the generally tangential line of the first and second tangential bores to engage the spacer member and tighten the spacer member in the vessel groove.

7. The vessel according to claim 6 wherein the spacer member includes an annular groove formed on a circumference of the spacer member outer surface and opening outwardly with respect to the vessel wall.

8. The vessel according to claim 7 comprising an elastomeric component disposed in the annular groove.

9. The vessel according to claim 6 wherein at least one of the tangential bores includes a threaded section, and the fastening element is threaded for mating engagement with the threaded section.

10. A vessel centering system comprising:

(a) a vessel having a central longitudinal axis and comprising an outer surface facing away from the longitudinal axis and a vessel groove, the vessel groove formed on a circumference of the vessel outer surface and opening away from the longitudinal axis;

(b) an annular ring member fitted in the vessel groove and extending outwardly with respect to the vessel to an outer ring surface, the ring member comprising first and second opposing lateral end surfaces defining a ring spacing therebetween;

(c) a fastening element engaging the first and second lateral end surfaces and extending across the ring spacing; and (d) a radial extension element disposed in contact with the outer ring surface.

11. The vessel centering system according to claim 10 wherein the ring member has a tangential bore extending along a line generally tangential to a curvature of the ring member, and the fastening element is disposed in the tangential bore.

12. The vessel centering system according to claim 10 wherein the ring member includes an outer surface and an annular groove formed in the ring member outer surface, and the radial extension element is an elastomeric component disposed in the ring member annular groove.

13. The vessel centering system according to claim 10 wherein the radial extension element is an elastomeric component.

14. The vessel centering system according to claim 10 comprising a vessel plate, wherein the radial extension element includes a plurality of bearings supported by the vessel plate and biased inwardly toward the ring member.

15. The vessel centering system according to claim 10 wherein the radial extension element includes a plurality of bearings supported by the ring member and biased outwardly from the ring member.

16. A vessel centering system comprising:

(a) a vessel having a central longitudinal axis and comprising an outer surface facing away from the longitudinal axis and a vessel groove, the vessel groove formed on a circumference of the vessel outer surface and opening away from the longitudinal axis;

(b) an annular ring member fitted in the vessel groove and extending outwardly with respect to the vessel to an outer ring surface, the ring member terminating at first and second lateral end surfaces defining a ring spacing therebetween;

(c) a fastening element engaging the ring member and extending across the ring spacing; and (d) an elastomeric element disposed in contact with the outer ring surface.

17. The vessel centering system according to claim 16 wherein the ring member comprises an annular groove formed in the outer ring surface, and the elastomeric element is disposed in the ring member annular groove.

18. A vessel centering system comprising:

(a) a vessel including an outer surface and a vessel groove formed on a circumference of the vessel outer surface;

(b) an annular ring member fitted in the vessel groove and extending outwardly with respect to the vessel, the ring member terminating at first and second lateral end surfaces defining a ring spacing therebetween;

(c) a fastening element engaging the ring member and extending across the ring spacing; and (d) a plurality of bearings disposed in contact with the ring member.

19. A vessel comprising:

(a) a vessel wall comprising an outer surface arid a vessel groove formed on a circumference of the vessel outer surface;

(b) an annular; spacer member fitted in the vessel groove and extending outwardly with respect to the vessel wall, the spacer member terminating at a gap defined by a first lateral end surface and a second lateral end surface of the spacer member;

(c) a fastening element engaging the spacer member at the first and second lateral end surfaces; and (d) a plurality of biased bearings attached to the spacer member.

* * * * *